US007259369B2

(12) United States Patent
Scott et al.

(10) Patent No.: US 7,259,369 B2
(45) Date of Patent: Aug. 21, 2007

(54) DUAL MODE ION MOBILITY SPECTROMETER AND METHOD FOR ION MOBILITY SPECTROMETRY

(75) Inventors: Jill R. Scott, Idaho Falls, ID (US); David A. Dahl, Idaho Falls, ID (US); Carla J. Miller, Idaho Falls, ID (US); Paul L. Tremblay, Idaho Falls, ID (US); Timothy R. McJunkin, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 168 days.

(21) Appl. No.: 11/209,534

(22) Filed: Aug. 22, 2005

(65) Prior Publication Data

US 2007/0040111 A1    Feb. 22, 2007

(51) Int. Cl.
*H01J 49/40* (2006.01)
*H01J 49/28* (2006.01)
*H01J 49/00* (2006.01)

(52) U.S. Cl. .................. 250/287; 250/281; 250/282; 250/283; 250/299; 313/359.1

(58) Field of Classification Search ............... 250/287
See application file for complete search history.

(56) References Cited

U.S. PATENT DOCUMENTS

| | | | | |
|---|---|---|---|---|
| 4,445,038 A * | 4/1984 | Spangler et al. | ............ | 250/382 |
| 6,888,130 B1 * | 5/2005 | Gonin | ........................ | 250/287 |
| 7,005,632 B2 * | 2/2006 | Miller et al. | ................ | 250/287 |
| 7,045,776 B2 * | 5/2006 | Kaufman et al. | ........... | 250/281 |
| 7,119,328 B2 * | 10/2006 | Kaufman et al. | ........... | 250/281 |
| 7,157,700 B2 * | 1/2007 | Kaufman et al. | ........... | 250/286 |
| 2003/0052263 A1 * | 3/2003 | Kaufman et al. | ........... | 250/281 |
| 2003/0141446 A1 * | 7/2003 | Blanchard | .................... | 250/287 |
| 2004/0094704 A1 * | 5/2004 | Miller et al. | ................ | 250/287 |
| 2005/0199799 A1 * | 9/2005 | Takada et al. | .............. | 250/288 |
| 2006/0060768 A1 * | 3/2006 | Kaufman et al. | ........... | 250/281 |
| 2007/0040111 A1 * | 2/2007 | Jill et al. | .................... | 250/287 |

* cited by examiner

*Primary Examiner*—Nikita Wells
*Assistant Examiner*—Bernard Souw
(74) *Attorney, Agent, or Firm*—Fennemore Craig P.C.

(57) ABSTRACT

Ion mobility spectrometer apparatus may include an ion interface that is operable to hold positive and negative ions and to simultaneously release positive and negative ions through respective positive and negative ion ports. A first drift chamber is operatively associated with the positive ion port of the ion interface and encloses an electric field therein. A first ion detector operatively associated with the first drift chamber detects positive ions from the first drift chamber. A second drift chamber is operatively associated with the negative ion port of the ion interface and encloses an electric field therein. A second ion detector operatively associated with the second drift chamber detects negative ions from said second drift chamber.

17 Claims, 7 Drawing Sheets

DUAL MODE ION MOBILITY SPECTROMETER AND METHOD FOR ION MOBILITY SPECTROMETRY

CONTRACTUAL ORIGIN OF THE INVENTION

The United States Government has certain rights in this invention pursuant to Contract No. DE-AC07-05ID14517 between the United States Department of Energy and Battelle Energy Alliance, LLC.

TECHNICAL FIELD

This invention relates to ion mobility spectrometry in general and more specifically to ion mobility spectrometry methods and ion mobility spectrometers having improved sensitivities.

BACKGROUND

Ion mobility spectrometry is a technique that separates and detects electrically charged particles (e.g., ions) that have been sorted according to how fast they travel through an electrical field in a chamber containing a gas, typically at atmospheric pressure. Small ions travel through the gas faster than do large ions and reach the end of the chamber first, with successively larger ions arriving later. Because ion mobility spectrometry only sorts ions by size, and not by their chemical properties or other identifying features, it cannot be used in all cases to make a positive identification of unknown compounds. However, ion mobility spectrometers can be used with certain compounds and can make measurements quite rapidly (e.g., in only a few seconds), therefore making them highly desirable for use in certain applications. For example, ion mobility spectrometers are commonly used to detect explosives, narcotics, and chemical warfare (e.g., nerve and blister) agents.

A typical ion mobility spectrometer comprises an ionization region, a drift chamber, and a detector. The ionization region is located at one end of the drift chamber, while the detector is located at the other end of the drift chamber. The ionization region is typically provided with a radioactive source, such as $^{63}$Ni, suitable for ionizing the sample material, although other ionizing techniques may be used. Ions of the sample material from the ionization region are introduced into the drift chamber, whereupon they ultimately reach the detector at the far end. The arriving ions cause the detector to generate electrical pulses which may thereafter be interpreted to form a conclusion about the nature of the sample material.

While ion mobility spectrometers of the type just described work well and are being used, they are not without their disadvantages. For example, ion mobility spectrometers having a single drift chamber cannot readily be used with both positive and negative ions, which limits the utility of such spectrometers. For example, while spectrometers that work with positive ions are useful for detecting drugs, nerve agents, and some types of explosives, they are not effective in detecting most types of explosives and blister agents, because such materials are better characterized by detecting the negatively charged ions they produce. Consequently, two separate spectrometers (e.g., both a positive ion type and a negative ion type) must be used in order to detect both classes of materials.

Partly in an effort to address this limitation, so-called "dual mode" ion mobility spectrometers have been developed. Dual mode ion mobility spectrometers utilize two drift chambers. Thus, a single spectrometer can be used to detect both positive and negative ions. Unfortunately, however, most dual mode ion mobility spectrometers cannot provide for the simultaneous detection of both positive and negative ions. Instead, such designs operate in a pulsed mode, wherein the spectrometer alternately detects positive ions, then negative ions. While dual mode ion mobility spectrometers have been developed that can simultaneously detect both positive and negative ions, they typically require complex apparatus for separating the positive and negative ions before they enter the drift chambers. In addition, such separation apparatus also tends to decrease the sensitivities of the spectrometers that utilize them.

Consequently, a need remains for an ion mobility spectrometer and ion mobility spectrometry method that can simultaneously detect both positive and negative ions, but without the disadvantages associated with prior art systems. Additional advantages could be realized if such an improved ion mobility spectrometer and method provided for increased detection limits and resolution.

SUMMARY OF THE INVENTION

Ion mobility spectrometer apparatus may comprise an ion interface that is operable to hold positive and negative ions and to simultaneously release positive and negative ions through respective positive and negative ion ports. A first drift chamber is operatively associated with the positive ion port of the ion interface and encloses an electric field therein. A first ion detector operatively associated with the first drift chamber detects positive ions from the first drift chamber. A second drift chamber is operatively associated with the negative ion port of the ion interface and encloses an electric field therein. A second ion detector operatively associated with the second drift chamber detects negative ions from said second drift chamber.

A method for performing ion mobility spectrometry may comprise: Holding positive and negative ions in a holding region; simultaneously releasing positive and negative ions from the holding region into respective first and second drift tubes; detecting positive ions arriving at a distal end of the first drift tube; and detecting negative ions arriving at a distal end of the second drift tube.

BRIEF DESCRIPTION OF THE DRAWING

Illustrative and presently preferred embodiment of the invention are shown in the accompanying drawing in which.

DETAILED DESCRIPTION OF THE PREFERRED EMBODIMENTS

Figure 1:
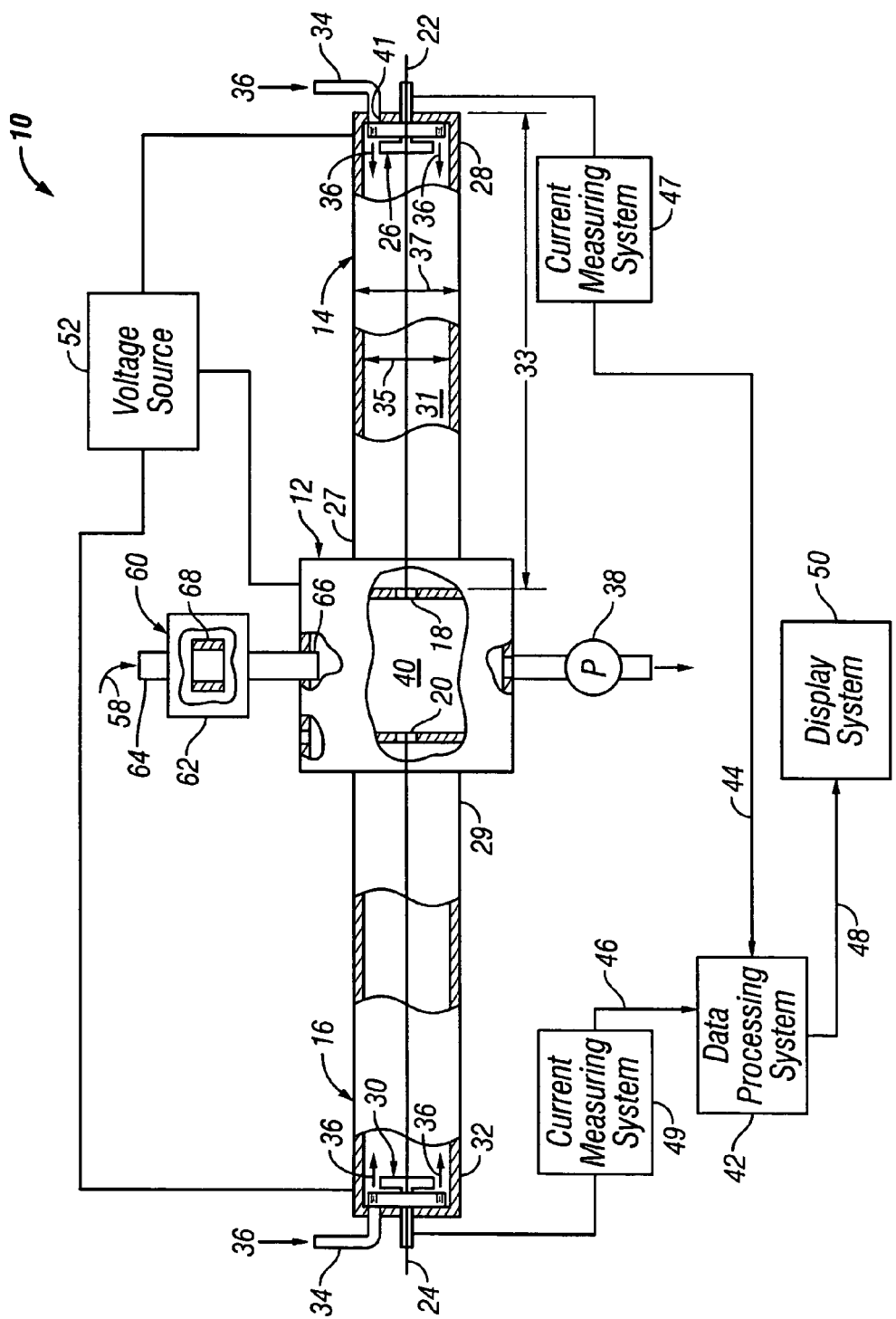
FIG. 1 is a schematic representation of one embodiment of an ion mobility spectrometer with portions thereof broken away to show certain interior features of the ion mobility spectrometer.

An ion mobility spectrometer 10 according to one embodiment of the invention is illustrated in FIG. 1 and may be used in accordance with the teachings provided herein to simultaneously process both positive and negative ions that may be produced by the sample material being analyzed. Briefly, the ion mobility spectrometer 10 may comprise an ion interface 12 having first and second drift chambers 14 and 16 extending therefrom. The ion interface 12 is operable to hold positive and negative ions (not shown) and to simultaneously release (i.e., allow) into the drift chambers 14 and 16 the positive and negative ions through respective positive and negative ion ports 18 and 20 provided in the ion interface 12.

More specifically, the first drift chamber 14 is operatively associated with the positive ion port 18 of the ion interface 12 and receives positive ions from the ion interface 12. The second drift chamber 16 is operatively associated with the negative ion port 20 of the ion interface 12 and receives negative ions from the ion interface 12. The first and second drift chambers 14 and 16 enclose respective electric fields that, in one embodiment, vary linearly along axes 22 and 24 of the respective first and second drift chambers 14 and 16. A first ion detector 26 positioned at a distal end 28 of first drift chamber 14 detects positive ions arriving at the distal end 28 of first drift chamber 14. A second ion detector 30 positioned at a distal end 32 of the second drift chamber 16 detects negative ions arriving at the distal end 32 of second drift chamber 16.

As will be described in greater detail below, the ion mobility spectrometer 10 may be provided with one or more carrier gas inlets 23 for introducing one or more carrier gases (represented by arrow 25) into the ion interface 12. See FIG. 2. In addition, the ion mobility spectrometer 10 may also be provided with one or more drift gas inlets 34 for introducing one or more drift gases (represented by arrows 36) into the first and second drift chambers 14 and 16 of the ion mobility spectrometer 10. See FIG. 1.

It is generally preferred, but not required, that the ion mobility spectrometer 10 may also be provided with a pump 38. Such an optional pump 38 may be used to exhaust the carrier gases 25 and drift gases 36 from the interior 40 of the ion mobility spectrometer 10 and to maintain the interior 40 within a range of pressures suitable for performing ion mobility spectrometry in accordance with the teachings provided herein. Alternatively, such a pump 38 could be omitted and the ion mobility spectrometer 10 operated at substantially atmospheric pressure. If no pump (e.g., pump 38) is used, the ion mobility spectrometer 10 may be provided with one or more vents (not shown) to prevent the build-up of pressure within the interior region 40 of ion mobility spectrometer 10.

A data processing system 42 operatively associated with the first and second ion detectors 26 and 30 receives output signals 44 and 46 from respective current measuring systems 47 and 49 associated with the first and second ion detectors 26 and 30. The data processing system 42 processes the output signals 44 and 46 to produce output data 48. In one embodiment, output data 48 may be presented on a suitable display system 50, although other arrangements are possible.

A voltage source 52 operatively connected to the ion interface 12 and to the first and second drift chambers 14 and 16 is used to provide various voltage functions to the ion interface 12 and to the first and second drift chambers 14 and 16 in the manner that will be described in greater detail below. Briefly, the voltage source 52 may be operated to apply to various electrodes of the ion interface 12 at least an ion-confining voltage function and an ion release voltage function. The ion-confining voltage function results in the formation of a quadrupolar electric field 54 (FIG. 4) within the ion interface 12. The quadrupolar electric field 54 confines both positive and negative ions within the ion interface 12. The ion release voltage function results in the formation of a linear electric field 56 within the ion interface 12. See FIG. 5. The linear electric field 56 causes the positive and negative ions that were previously confined by the quadrupolar electric field 54 to be substantially simultaneously released through the positive and negative ions ports 18 and 20, respectively. See FIG. 1.

Figure 6:
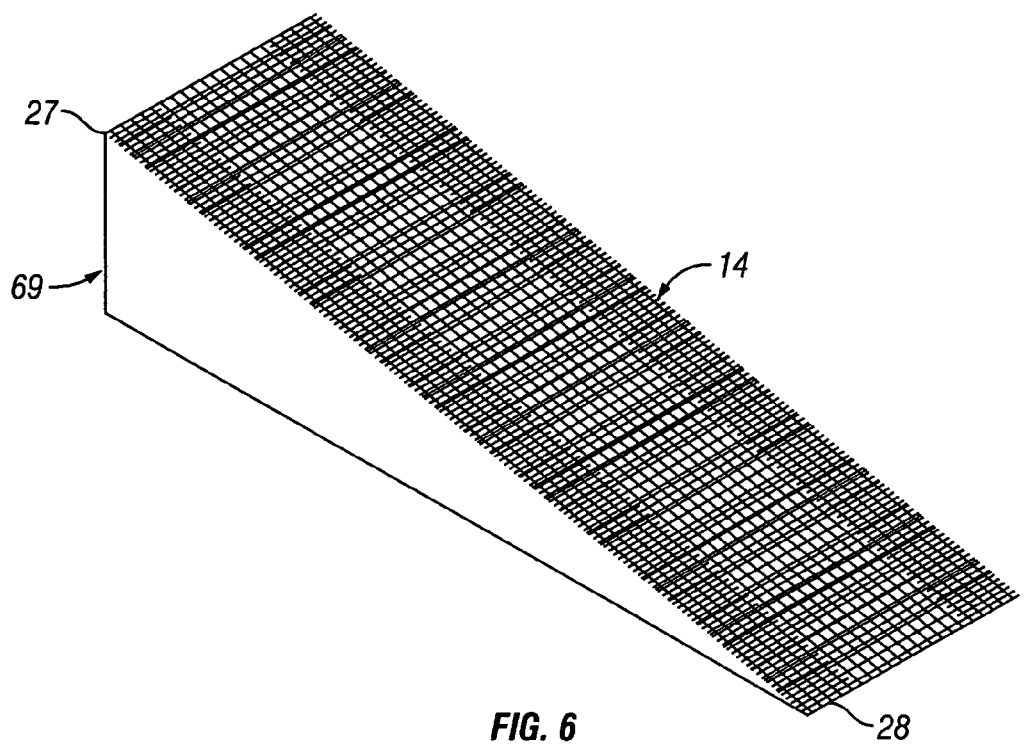
FIG. 6 is a computer-generated plot of a linear electric field that may be produced within a first embodiment of the ion drift chamber.

The voltage source 52 may also be used to apply voltage potentials across the first and second drift chambers 14 and 16 to create or form the electric fields within the first and second drift chambers 14 and 16. In one embodiment, the first and second drift chambers 14 and 16 are fabricated from an electrically resistive material, such as ferrite or graphite, so that the electrical resistance of the drift chambers 14 and 16 varies substantially linearly along the axes 22 and 24 of the respective drift chambers 14 and 16. The linear variation in the electrical resistance of the drift chambers 14 and 16 causes the electric fields produced within the drift chambers 14 and 16 to also vary substantially linearly along the respective axes 22 and 24 of first and second drift chambers 14 and 16. See FIG. 6. Alternatively, and as will be described in greater detail below, if the drift chambers (e.g., 14 and 16) are constructed in a different manner, the resulting electric fields produced within the drift chambers may vary in a non-linear manner along the lengths thereof.

The ion mobility spectrometer 10 may be operated as follows to perform ion mobility spectrometry in accordance with the methods described herein. Assuming a suitable sample has been collected, gaseous constituents (represented by arrow 58) of the sample are ionized within an ionization chamber 60. In one embodiment, the ionization chamber 60 comprises a separate component. Alternatively, and as will be described in greater detail below, the sample may be ionized within the ion interface 12 itself. The gaseous constituents 58 of the sample will commonly result in the formation of both positive and negative ions. However, certain gaseous constituents 58 may result in the formation of exclusively either positive ions or negative ions. Regardless of whether the gaseous constituents 58 result in the formation of positive ions, negative ions, or more commonly a combination of both positive and negative ions, ions (not shown) formed within the ionization chamber 60 are then allowed to enter the ion interface 12. The voltage source 52 is operated to apply the ion-confining voltage function to the ion interface 12 to confine the ions within the ion interface 12. More specifically, the ion-confining voltage function results in the formation of the quadrupolar electric field 54

(FIG. 4) within the ion interface 12 which 54 confines both positive and negative ions within the ion interface 12.

At the appropriate time, the voltage source 52 may be operated to instead apply the ion release voltage function to the ion interface 12. The ion release voltage function causes the quadrupolar electric field 54 to change to the linear electric field 56 (FIG. 5), resulting in the substantially simultaneous release of both positive and negative ions from the ion interface 12. That is, positive ions are released through the positive ion port 18 into the first drift chamber 14, whereas negative ions are released through the negative ion port 20 into the second drift chamber 16 at substantially the same time.

Upon entering the drift chambers 14 and 16, the respective positive and negative ions travel toward the respective distal ends 28 and 32 of the drift chambers 14 and 16 under the influence of the electric fields enclosed thereby. Positive ions reaching the distal end 28 of first drift chamber 14 are detected by the first ion detector 26, whereas negative ions reaching the distal end 32 of second drift chamber 16 are detected by the second ion detector 30. The data processing system 42 receives output signals 44 and 46 from respective current measuring systems 47 and 49 operatively associated with the first and second ion detectors 26 and 30 and processes them to produce output data 48. Thereafter, output data 48 may be presented on display system 50.

One advantage of the ion mobility spectrometer according to the present invention is that it is capable of simultaneously detecting both positive and negative ions. Consequently, a single ion mobility spectrometer can be used to detect a wide range of substances that may be characterized by both positive and negative ions. In addition, the ability to retain and simultaneously release both positive and negative ions from a single location (i.e., the ion interface) ameliorates some of the problems associated with prior art systems, such as reduced sensitivity. Still other advantages are associated with the drift chambers. For example, drift chambers involving linear electric fields, i.e., electric fields that vary in a linear manner, reduce both the radial and axial dispersion of ions as they move along the drift chambers. Consequently, sensitivity, detectability, and resolution of ions of nearly the same size are substantially improved.

Having briefly described one embodiment of the ion mobility spectrometer of the present invention, as well as some of its more significant features and advantages, the various embodiments of the ion mobility spectrometer and method for conducting ion mobility spectrometry will now be described in detail.

Referring back now to FIG. 1, a first embodiment 10 of an ion mobility spectrometer according to the present invention may comprise an ion interface 12 suitable for holding both positive and negative ions and then substantially simultaneously releasing the ions in the manner that was briefly described above. In one embodiment, the ions may be provided to the ion interface 12 by a suitable ion source 60, although a separate ion source is not required. For example, ions could be generated or produced within the ion interface 12 by techniques such as electron ionization, photo ionization including laser ionization, or chemical ionization.

If a separate ion source 60 is used, then ion source 60 may comprise an ionization chamber 62 having an inlet end 64 and an outlet end 66. The inlet end 64 of ionization chamber 62 may be configured to receive the gaseous constituents 58 of the sample being tested. The outlet end 66 is positioned at about the middle of the ion interface 12 (i.e., substantially midway between the two ends 72 and 74 of ion interface 12) so that positive and negative ions from the ion source 60 may be introduced into the interior region 40 of ion interface 12, as best seen in FIG. 1. The ionization chamber 62 may also be provided with an ionization agent 68 suitable for ionizing the gaseous constituents 58 of the sample. In one embodiment, the ionization agent 68 comprises a radioactive isotope (e.g., $^{63}$Ni). Alternatively, other ionization techniques are known and could also be used. Consequently, the present invention should not be regarded as limited to any particular technique (e.g., the use of a radioactive isotope) to ionize the gaseous constituents 58 of the sample material.

The ion interface 12 is operatively associated with the ion source 60 and receives positive and negative ions from the gaseous constituents 58 of the particular sample being tested. As mentioned above, most samples will result in the formation of both positive and negative ions, and both positive and negative ions will be delivered to the interior region 40 of the ion interface 12. However, it should be noted that certain sample materials may result in the formation of either positive ions alone or negative ions alone. Consequently, the terms "ion" and "ions" as used herein includes positive ions, negative ions, and mixtures thereof.

Proceeding now with the description, in one embodiment, the ion interface 12 may be substantially identical to the electrostatic shape shifting ion optics device that is shown and described in U.S. patent application Ser. No. 11/021,380, filed Dec. 23, 2004, and entitled "Electrostatic Shape-Shifting Ion Optics," which is incorporated herein by reference for all that it discloses. A brief summary of the material disclosed in that patent application is provided herein in order to provide a better background for understanding the ion interface 12 of the present invention.

Figure 2:
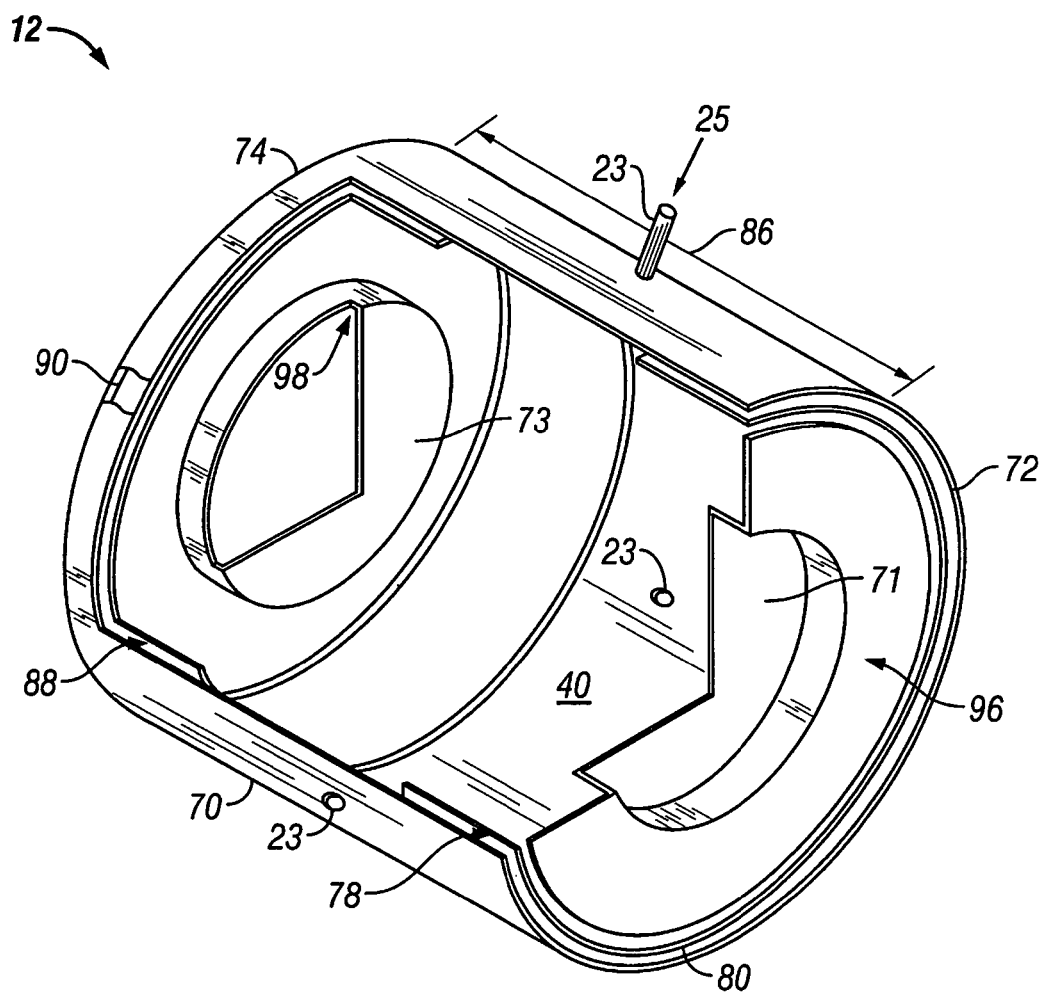
FIG. 2 is a cut-away view in perspective the ion interface of the ion mobility spectrometer illustrated in FIG. 1.
Figure 3:
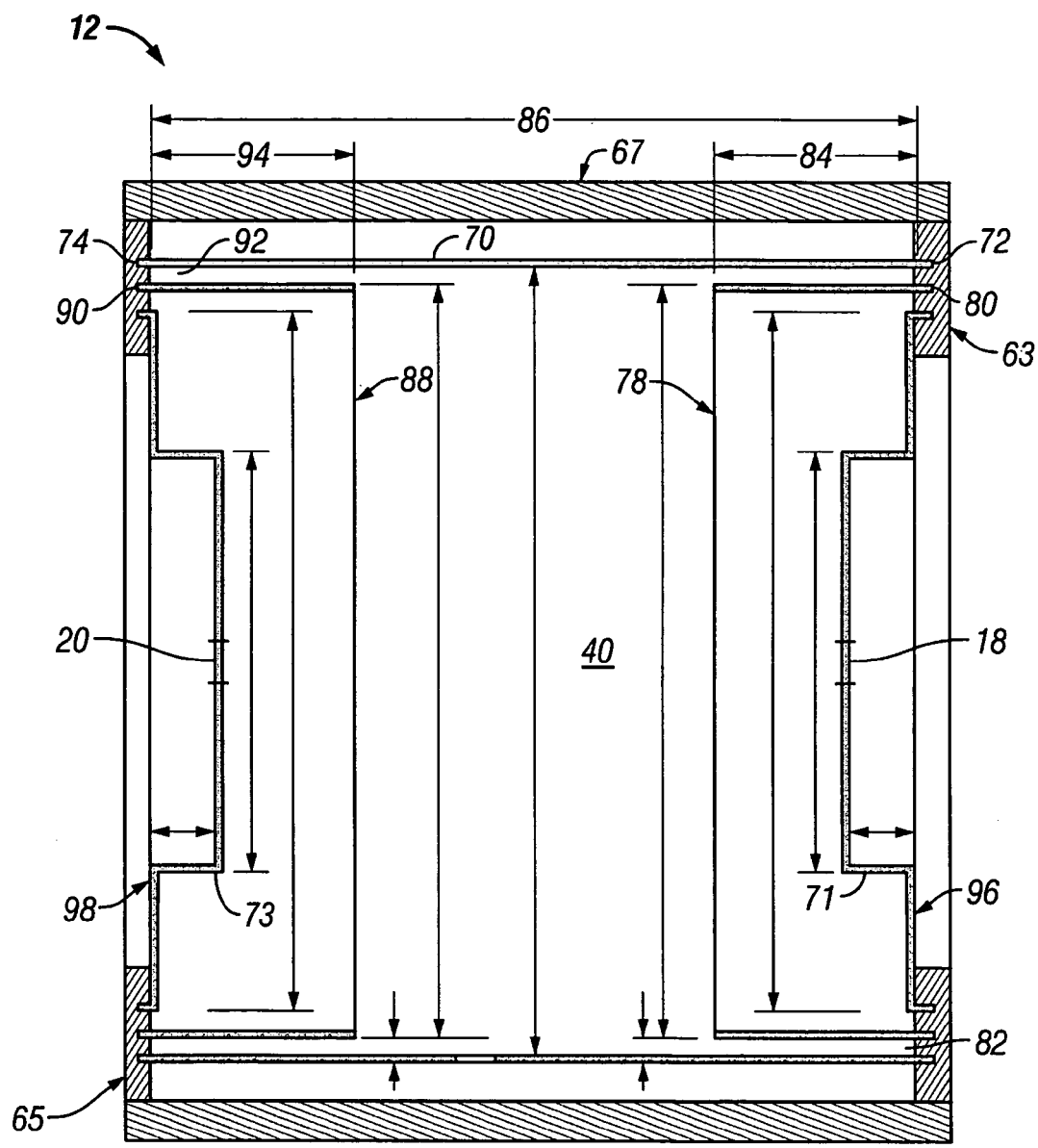
FIG. 3 is a sectional view in elevation of the ion interface illustrated in FIG. 1.

Referring now primarily to FIGS. 1-3, the ion interface 12 utilized in one embodiment of the present invention may comprise a generally cylindrically-shaped outer electrode 70 having first and second open ends 72 and 74. The outer electrode 70 may be provided with at least one, and generally a plurality of inlets or openings 23 therein to allow a carrier gas 25 to be introduced into the interior region 40 of the ion interface 12. See FIGS. 1 and 3. In the embodiment shown and described herein, three (3) inlets or openings 23 are provided in the ion interface 12. The openings 23 are provided about midway between the two ends 72 and 74 of ion interface 12 and are spaced about 120□ apart. Such an arrangement allows the carrier gas 25 to be more evenly introduced into the interior region 40 than if only a single opening 23 were provided. The inlets or openings 23 provided in the ion interface 12 may be left open or may be covered by electro-formed wire-mesh screen (not shown).

The carrier gas 25 may comprise any of a wide range of gases suitable for the particular application, and the present invention should not be regarded as limited to any particular type of gas. Generally speaking, non-reactive gases, such as dry nitrogen, may be used for the carrier gas 25, although reactive gases, such as air, ammonia, or NO could also be used. Alternatively, the carrier gas 25 may comprise a mixture of non-reactive and reactive gases.

The outer electrode 70 may comprise any of a wide range of sizes, depending on the particular application, so long as the scaling rules described in U.S. patent application Ser. No. 11/021,380 are followed. Consequently, the present invention should not be regarded as limited to an outer electrode 70 having any particular size. However, by way of example, in one embodiment, the outer electrode 70 has an inside diameter of about 126 mm and a length 86 of about 120 mm.

The outer electrode 70 may be fabricated from any of a wide range of electrically conductive materials (e.g., metals and metal alloys) suitable for the intended application. Consequently, the present invention should not be regarded as limited to an outer electrode 70 fabricated from any particular material. However, it is generally preferred that the electrically conductive material not form an insulating surface layer of the type formed on many metals, such as aluminum. By way of example, in one embodiment, the outer electrode 70 is formed from a stainless steel alloy. The thickness of the particular material used to form the outer electrode 70 is also not particularly critical, but it is generally preferred that the wall thickness of the outer electrode 70 not exceed about 5-10 mm. By way of example, in one embodiment, the wall thickness of the material used to form the outer electrode 70 is about 1 mm.

In addition, it is important to note that the outer electrode 70 need not be formed from a sheet-like (e.g., solid) material, but could instead be formed from an electrically conductive screen or screen-like material (e.g., electro-formed screen), as disclosed in the patent application referenced above. Consequently, the outer electrode 70 should not be regarded as limited to any particular type of material (e.g., conductive metals or metal alloys) having any particular configuration (e.g., solid, sheet-like configurations, or screen-like configurations).

A first inner electrode 78 comprising a generally cylindrically-shaped structure is positioned within the interior 40 defined by the outer electrode 70 so that an open end 80 of first inner electrode 78 is substantially aligned with the first open end 72 of outer electrode 70. The first inner electrode 78 is made to be somewhat smaller than the outer electrode 70 so that an annular gap 82 is created between the outer electrode 70 and the first inner electrode 78. The length 84 of the first inner electrode 78 is considerably less than the length 86 of the outer electrode 70.

A second inner electrode 88, also comprising a generally cylindrically-shaped structure is positioned within the interior 40 defined by the outer electrode 70 so that an open end 90 of the second inner electrode 88 is substantially aligned with the second open end 74 of the outer electrode 70. The second inner electrode 88 is made to be somewhat smaller than the outer electrode 70 so that an annular gap 92 is created between the outer electrode 70 and the second inner electrode 88. The length 94 that is considerably less than the length 86 of the outer electrode 70 and is about equal to the length 84 of the first inner electrode 78.

The dimensions of the first and second inner electrodes 78 and 88 are related the dimensions of the outer electrode 70 and to the shapes of the electric fields that are desired to be produced therein, as described in U.S. patent application Ser. No. 11/021,380. Thus, the first and second inner electrodes 78 and 88 may comprise any of a wide range of dimensions. However, by way of example, in one preferred embodiment, the first and second inner electrodes 78 and 88 are substantially identical, having outside diameters of about 120 mm and lengths of about 31 mm. Thus, the annular gaps 82 and 92 are about 3 mm.

The ion interface 12 also comprises first and second end cap electrodes 96 and 98. The first and second end cap electrodes 96 and 98 are positioned at about each respective open end 72 and 74 of the outer electrode 70. Each end cap electrode 96, 98 is provided with a respective stepped portion 71, 73 therein that extends into the interior 40 of the ion interface 12. The stepped portions 71, 73 modify or alter the electric field that is produced within the interior 40 of the ion interface when the voltage functions are applied to the various electrodes 70, 78, 88, 96, and 98 in the manner described herein. In addition, the stepped portions 71 and 73 also receive the drift chambers 14 and 16, as best seen in FIG. 1. The stepped portions 71 and 73 of respective first and second end cap electrodes 96 and 98 are provided with openings therein that form the positive and negative ion ports 18 and 20.

In the embodiment shown and described herein, both the first and second end cap electrodes 96 and 98 are substantially identical and have outside diameters of about 112 mm. The stepped portions 71 and 73 of respective first and second end cap electrodes 96 and 98 have diameters of about 68 mm. The off-sets of the stepped portions 71 and 73 are about 10 mm That is, the stepped portions 71 and 73 extend inwardly into the interior 40 of the ion interface 12 by a distance of about 10 mm.

The various electrodes 78, 88, 96, and 98 comprising the ion interface 12 may be fabricated from any of a wide range of electrically conductive materials (e.g., metals and metal alloys) suitable for the intended application. Alternatively, the various electrodes 78, 88, 96, and 98 may be fabricated from wire-mesh screen (e.g., electro-formed wire-mesh screen) Consequently, the present invention should not be regarded as limited to electrodes fabricated from any particular materials. However, it is generally preferred that the electrically conductive material not form an insulating surface layer of the type formed on many metals, such as aluminum. By way of example, in one embodiment, the various electrodes 78, 88, 96, and 98 are fabricated from stainless steel. The various electrodes 78, 88, 96, and 98 may be secured to the outer electrode 70 by means of insulating end plates 63 and 65 and an insulating main body portion 67, as best seen in FIG. 3.

Each of the electrodes 70, 78, 88, 96, and 98 comprising the ion interface 12 are connected to the voltage source 52. As discussed above, the voltage source 52 is used to apply voltage functions to each of the various electrodes 70, 78, 88, 96, and 98 in order to produce or create electric fields within the interior 40 of ion interface 12 that are suitable for confining ions within the interior region 40 and for substantially simultaneously releasing ions from the interior region 40 and into the first and second drift chambers 14 and 16. In this regard it should be noted that it is generally preferred, but not required, that the voltage source 52 be capable of independently controlling the particular voltage functions that are applied to each of the electrodes 70, 78, 88, 96, and 98 to allow maximum control over the resulting electric field.

The voltage source 52 may comprise any of a wide range of voltage sources, such as computer-controlled voltage sources, that are now known in the art or that may be developed in the future that are or would be suitable for providing the voltage functions to the electrodes in the manner described herein. In addition, because suitable voltage sources are known in the art and could be easily supplied by persons having ordinary skill in the art after having become familiar with the teachings provided herein, the particular voltage source 46 that may be utilized in one embodiment of the present invention will not be described in greater detail herein.

The particular voltage functions required to produce the desire electric field, e.g., the quadrupolar electric field 54 (FIG. 4) and the linear electric field 54 (FIG. 5), may be determined with the aid of a computer program to model the electric field that would result from a given electrode geometry and for given applied voltage functions. Such a computer modeling process can be used to determine those modifications of the shapes of the electrodes and/or the voltage functions that may be applied to the electrodes in order to generate the desired electric fields.

The ion interface 12 having the electrode configurations described above may be used to generate a quadrupolar electric field 54 (FIG. 4) suitable for confining ions, as well as a linear electric field 56 (FIG. 5) suitable for substantially simultaneously releasing ions from the ion interface 12. The electric field can be changed from quadrupolar to linear and back again by simply changing the voltage functions that are applied by the voltage source 52 to the various electrodes 70, 78, 88, 96, and 98.

Figure 4:
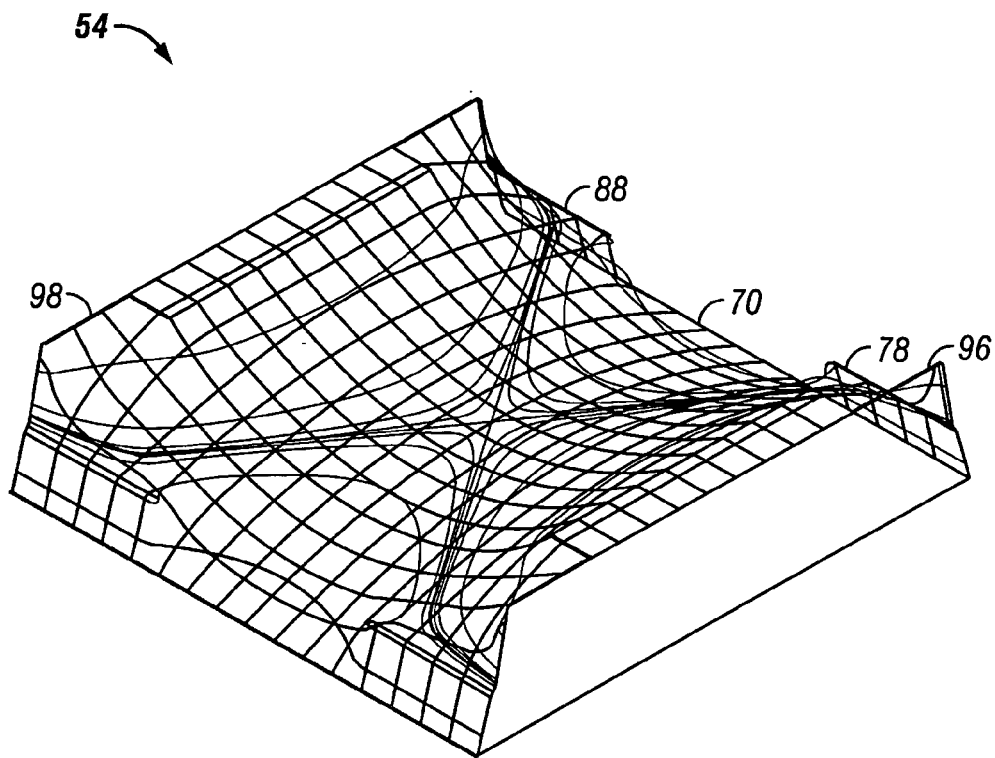
FIG. 4 is a computer-generated plot of a quadrupolar electric field that may be produced within the ion interface.

For example, and with reference now to FIG. 4, the voltage functions applied to the various electrodes 70, 78, 88, 96, and 98 of the ion interface 12 may be selected to produce a quadrupolar electric field 54 suitable for confining ions therein. The electric field depicted in FIG. 4 was generated by a computer modeling program known as "SIMION 7.0" which is available from Scientific Instruments Services, Inc., 1027 Old York Road, Ringoes, N.J. 08551 (USA). The computer modeling is based on the ion interface 12 having the electrode configurations and dimensions shown and described herein. The electric potentials (e.g., voltage functions) placed on the various electrodes have the relative potentials depicted in FIG. 4 by reference to the relative vertical positions of the various electrodes. Thus, the quadrupolar electric field 54 may be produced by placing the outer electrode 70 at a base potential. By way of example, the base potential may be a ground potential, although this is not required. The first and second end cap electrodes 96 and 98 are both placed at a more positive (i.e., higher) potential than the ground potential, with the first and second inner electrodes 78 and 88 together placed at an intermediate potential. By way of example, the intermediate potential may be approximately midway between the potential of outer electrode 70 and the potential of the first and second end cap electrodes 96 and 98.

Figure 5:
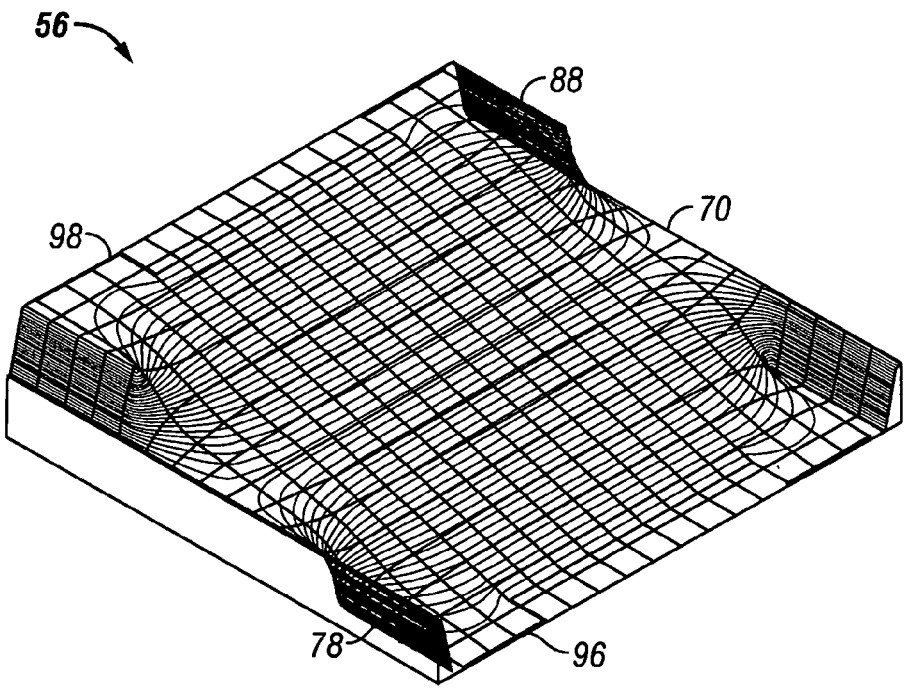
FIG. 5 is a computer-generated plot of a linear electric field that may be produced within the ion interface.

A linear electric field 56 suitable for substantially simultaneously releasing (i.e., allowing) positive and negative ions from the respective positive and negative ion ports 18 and 20 of ion interface 12 may be created by changing the voltage functions provided to the various electrodes 70, 78, 88, 96, and 98 comprising the ion interface 12. The linear electric field 56 depicted in FIG. 5 was also generated by the SIMION 7.0 computer modeling program and illustrates the shape of the electric field with the electrodes having the configurations and dimensions specified herein. The electric potentials (e.g., voltage functions) placed on the various electrodes have the relative potentials depicted in FIG. 5 by reference to the relative vertical positions of the various electrodes. Thus, the linear electric field 56 illustrated in FIG. 5 may be produced by placing the outer electrode 70 at a base potential. By way of example, the base potential may be a ground potential, although this is not required. The second inner electrode 88 and second end cap electrode 98 are placed at a more positive (i.e, higher) potential than the base potential. The first inner electrode 78 and the first end cap electrode 96 are placed at a more negative (i.e., lower) potential than the base potential. The magnitudes of the more positive (i.e., higher) and more negative (i.e., lower) potentials placed on various electrodes are substantially identical, so that the base potential of outer electrode 70 is substantially midway between the potentials placed on the other electrodes, as best seen in FIG. 5.

The electric field (e.g., quadrupolar field 54 or linear field 56) can be readily optimized for a particular operating regime (e.g., high or low-pressure) by simply varying (usually slightly) the voltage functions applied to the various electrodes 70, 78, 88, 96, and 98 comprising the ion interface 12. Suitable modifications to the voltage functions may be arrived at, for example, by using the computer modeling program (e.g., SIMION 7.0) to model the electric field shape that would result from modifications to the various voltage functions. Alternatively, other methods, such as analytical methods or even trial-and-error, could be used to arrive at the appropriate voltage functions.

Regardless of the particular type of electric field (e.g., quadrupolar field 54 or linear field 56) that is produced within the interior 40 of ion interface 12, it is important to recognize that the electric field can be rapidly changed or altered to cause the ions under the influence of the electric field to be manipulated or controlled as desired. For example, the quadrupolar electric field 54 (FIG. 4) may be used to confine radially injected ions within the interior 40 of ion interface 12. Then, the electric field may be rapidly changed to the linear electric field 56 (FIG. 5) to cause the ions to be axially ejected from one or both of the ion ports 18 and 20 provided in the respective end cap electrodes 96 and 98. See FIG. 1.

The first and second drift chambers 14 and 16 are operatively associated with the ion interface 12 and extend generally outwardly from the ion interface 12 as best seen in FIG. 1. In the embodiment shown and described herein, the first and second drift chambers 14 and 16 are identical, so only the first drift chamber 14 will be discussed in detail herein.

The first drift chamber 14 comprises a generally elongate, cylindrically shaped member having a proximal end 27, a distal end 28, and a length 33. The proximal end 27 of drift chamber 14 is operatively associated with the positive ion port 18 of the ion interface 12 so that the drift chamber 14 may receive positive ions ejected from the ion interface 12. More specifically, in the embodiment shown and described herein, the proximal end 27 of drift chamber 14 is sized to be received by the stepped portion 71 of first end cap electrode 96. Drift chamber 14 may also be provided with an opening 41 therein sized to receive the drift gas inlet 34.

The drift gas inlet 34 may be provided with an annular distribution ring 39 or other such device to allow the drift gas 36 to be distributed more evenly (e.g., in an annular fashion) into the distal end 28 of drift chamber 24. Alternatively, a plurality of openings 41 may be provided, with each such opening 41 being connected to the drift gas inlet 34, as would become apparent to persons having ordinary skill in the art after having become familiar with the teachings provided herein.

The first drift chamber 14 may be made to be any of a wide range of sizes depending on the particular application. Consequently, the present invention should not be regarded as limited to a drift chamber 14 having any particular size. However, by way of example, in one embodiment, the length 33 of first drift chamber 14 is selected to be about 15.55 cm. The inside diameter 35 is about 2.177 cm. The outside diameter 37 may be any convenient dimension. However, the difference between the inside diameter 35 and the outside diameter 37 establishes the wall thickness of the drift chamber 14, which may be required to be within a certain range, depending on the particular material used to fabricate the first drift chamber 14, as described below. By way of example, in one embodiment, the outside diameter 37 of drift chamber 14 is about 4.386 cm.

The first drift chamber 14 is fabricated from an electrically resistive material, such as a compressed ferrite or graphite powder, so that a voltage potential may be established along the axis 22 of drift chamber 14. The voltage potential results in the formation of an electric field within an interior region 31 defined by the first drift chamber 14.

It is generally preferred, but not required, that the electric field created within the interior region 31 of first drift chamber 14 be substantially linear along the axis 22 of drift chamber 14. See FIG. 6. The linear electric field 69 depicted in FIG. 6 was also generated by the SIMION 7.0 computer modeling program and illustrates the shape of the electric field with the drift chamber 14 having the configurations and dimensions specified herein. The electric potentials placed on the proximal and distal ends 27 and 28 of the drift chamber 14 have the relative potentials depicted in FIG. 6 by reference to the relative vertical positions of the proximal and distal ends 27 and 28 of the drift chamber 14. Thus, the linear electric field 69 illustrated in FIG. 6 may be produced by placing the distal end 28 at a potential that is lower than the potential placed on the proximal end 27. As mentioned, because, in the embodiment shown and described herein, the distal end 27 of drift chamber 14 is received by the stepped portion 71 of first end cap electrode 96 and is electrically connected thereto, the potential on the distal end 27 of the drift chamber 14 will be substantially equal to the potential placed on the first end cap electrode 96.

The potential between the proximal and distal ends 27 and 28 of the first drift chamber 14 may be selected to be within any of a wide range of potentials suitable for the intended application, as would become apparent to persons having ordinary skill in the art after having become familiar with the teachings provided herein. Consequently, the present invention should not be regarded as limited to any particular potential difference between the distal end 28 and the proximal end 27 of drift chamber 14. However, by way of example, in one embodiment, the distal end 28 of drift chamber 14 may be placed at about 1500 volts below ground potential, e.g., the potential of the outer cylindrical electrode 70 of the ion interface 12. The specific potential difference between the proximal end 27 and the distal end 28 will, of course, depend on the particular potential placed on the end cap electrode 96, and whether the ion interface 12 is being used to confine ions (FIG. 4) or release ions (FIG. 5).

As already briefly mentioned, such a linear electric field 69 can be created within the interior region 31 of drift chamber 14 by fabricating the drift chamber from an electrically resistive material (e.g., graphite or ferrite) and by placing a voltage potential across the drift chamber 14. Alternatively, an electrically resistive coating may be applied to the drift chamber 14, but it is usually difficult to make the electrically resistive coating even along the length of the drift chamber 14, which will result in non-linear variations of the electric field.

The strength of the electric field will vary as the electrical resistance of the material used to fabricate the drift chamber 14. Thus, if the electrical resistance of the material used to fabricate the drift chamber 14 varies linearly along the length of the drift chamber 14 (i.e., along axis 22 thereof), so will the electric field. Non-linear variations in the electrical resistance of the drift chamber 14 will result in corresponding non-linearities in the electric field.

Figure 7:
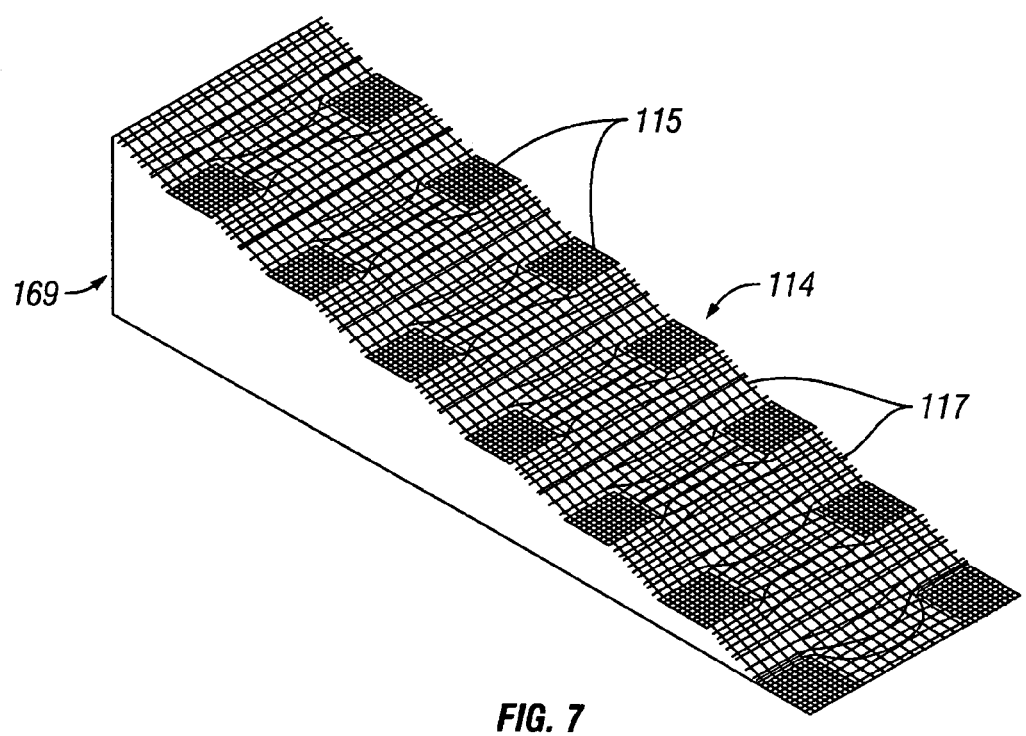
FIG. 7 is a computer-generated plot of a non-linear electric field that may be produced within a second embodiment of the ion drift chamber.
Figure 8:
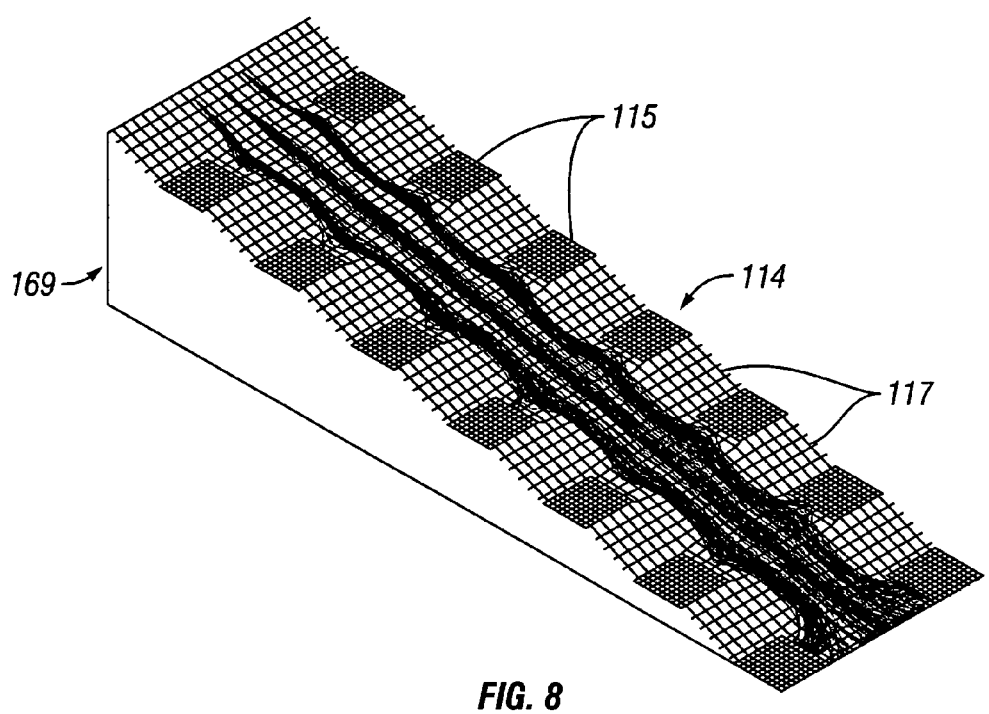
FIG. 8 is a computer-generated plot of radial ion paths within the non-linear electric field of the ion drift chamber of FIG. 7.
Figure 9:
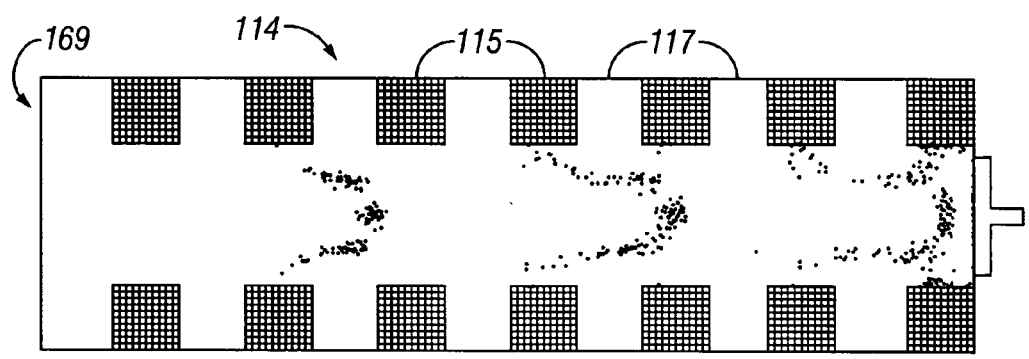
FIG. 9 is a computer-generated plot of axial distributions of ions within the non-linear electric field of the ion drift chamber of FIG. 7.

For example, and referring now to FIG. 7, another embodiment of a drift chamber 114 may involve a stacked arrangement of electrically conductive elements 115 separated by electrically resistive elements 117. Such an arrangement will produce a non-linear electrical field 169. While such a non-linear electrical field 169 may be useful in certain applications, it may result in an increase in the numbers of ions lost to the walls thereof, as shown in FIG. 8. Such a non-linear electric field 169 may also result in increased axial dispersion of the ions, as best seen in FIG. 9.

Figure 10:
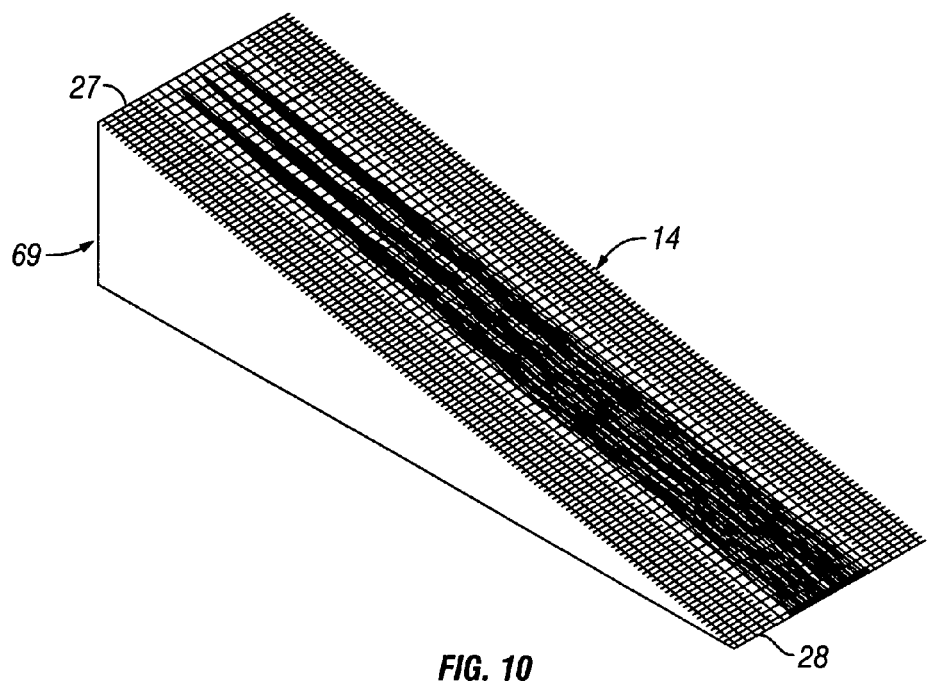
FIG. 10 is a computer-generated plot of radial ion paths within the linear electric field of the ion drift chamber of FIG. 6.
Figure 11:
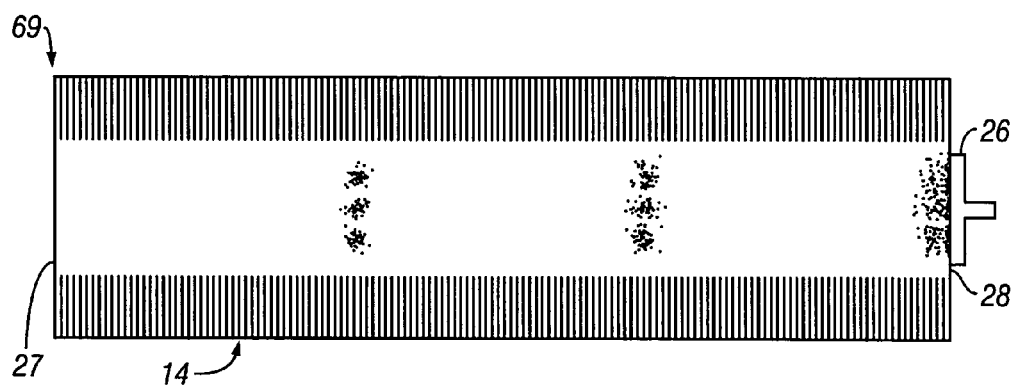
FIG. 11 is a computer-generated plot of axial distributions of ions within the linear electric field of the ion drift chamber of FIG. 6.

Referring now to FIG. 10, the linear electric field 69 (illustrated in FIG. 6) along the axis 22 of the first drift chamber 14 reduces the magnitude of radial ion drift as the ions move along the length 33 (FIG. 1) of the drift chamber 14 compared with the non-linear field 169 illustrated in FIG. 8. Accordingly, fewer ions will be absorbed by the walls of the drift tube 14, thereby resulting in increased sensitivity. The linear electric field 47 also reduces the axial dispersion of the ions that occurs as the ions move along the length of the drift chamber 14 (illustrated in FIG. 11) compared with the non-linear electric field 169 (illustrated in FIG. 9). Thus, the ions are more closely bunched together as they arrive at the detector 26, resulting in increased sensitivity and resolution of ions that are nearly the same size. In addition, the better ion control associated with the linear electric field 69 makes it easer for the data processing system 42 to detect the peak associated with the arrival of the ions at the detector. The ion tracks presented in FIGS. 8-11 were obtained with the SIMION 7.0 computer program described above for atmospheric pressure, as described in Appelhans, A. D.,; Dahl, D. A., "SIMION Ion Optics Simulations at Atmospheric Pressure," *International Journal of Mass Spectrometry* 2005, 244, 1-14, which is incorporated herein by reference for all that it discloses.

Referring back now to FIG. 1, the proximal end 27 of first drift chamber 14 is received by the stepped portion 71 of the first end cap electrode 96. In the embodiment shown and described herein, no insulator is used between the two components. Thus, the proximal end 27 of the first drift chamber 14 will be at the same electric potential as the first end cap electrode 96. The distal end 28 of first drift chamber 14 is electrically connected to the voltage source 52. Accordingly, the voltage source 52 may be used to apply the appropriate voltage potential along the length 33 of the first drift chamber 14.

The first detector 26 is provided within the distal end 28 of the first drift chamber 14 and is used to detect positive ions arriving at the distal end 28. The first detector 26 may comprise a generally plate-like member (e.g., a faraday plate), as illustrated in FIG. 1. Alternatively, the first detector 26 may comprise a cup-like member (e.g., a faraday cup). Because of the voltage potential existing along the length 33 of the first drift tube 14 may be substantial (e.g., about 1500 volts), the first detector 26 should be capable of operating at such potentials. By way of example, in one embodiment, the detector 26 is connected to a current measuring system 47 that is substantially identical to the current measuring system shown and described in U.S. Pat. No. 5,665,966, issued Sep. 9, 1997, and entitled "Current Measuring System," which is incorporated herein by reference for all that is disclosed therein. Alternatively, other systems known in the art or that may be developed in the future may also be used.

The second drift chamber 16 may be substantially identical to the first drift chamber 14, except that the potential placed on the distal end 32 thereof will be more positive (i.e., higher) than the potential placed on the proximal end 29 thereof in order to make the second drift chamber 16 suitable for processing negatively charged ions. Similarly, the second detector 30 may be substantially identical to the first detector 26 and may also comprise a current measuring system 49 of the type shown and described in U.S. Pat. No. 5,665,966.

As mentioned above, the ion mobility spectrometer 10 may also be provided with one or more gas inlets 23 and 34 for allowing gases, such as carrier gas 25 and drift gas 36, into the various interior regions of the ion mobility spectrometer 10. More specifically, and with reference now to FIG. 1, one embodiment of the ion mobility spectrometer 10 may be provided with carrier gas inlets 23 at the ion interface 12. Drift gas inlets 34 may be provided at the distal ends 28 and 32 of the respective first and second drift chambers 14 and 16. As mentioned above, the carrier gas 25 may comprise a non-reactive gas, such as dry nitrogen, although reactive gases (e.g., ammonia and NO) or mixtures of reactive and non-reactive gases may be used. The drift gas 36 may comprise a non-reactive gas, such as dry nitrogen, although other non-reactive gases may be used.

As briefly mentioned above, the ion mobility spectrometer 10 may be provided with a pump 38, although a pump 38 is not required. Generally speaking, providing the ion mobility spectrometer 10 with a pump 38 will allow the ion mobility spectrometer 10 at pressures below atmospheric. By way of example, in one embodiment, the pump 38 is fluidically connected to the ion interface 12 and is used to maintain the pressure within the ion mobility spectrometer 10 within a range of pressures suitable for performing ion mobility spectrometry in accordance with the teachings provided herein. In the embodiment shown and described herein, the pump 38 maintains the pressure within the ion mobility spectrometer 10 within a range of about 760 torr (e.g., atmospheric) to about 0.5 torr. Pump 38 may be provided with various ancillary systems or devices (not shown), e.g., pressure sensors, pump control systems, etc., to allow the pressure within the ion mobility spectrometer 10 to be maintained within the desired pressure range. However, because pumps, such as pump 38, as well as any other ancillary systems or devices required or desired to maintain the pressure within the ion mobility spectrometer 10 within a suitable range of pressures are well-known in the art and could be readily provided by persons having ordinary skill in the art after having become familiar with the teachings provided herein, the pump 38 and various ancillary systems or devices that may be used in conjunction therewith, will not be described in further detail herein.

If a pump 38 is not provided, then the ion mobility spectrometer 10 may be provided with suitable vent openings (not shown) to vent the carrier and drift gases 25 and 36 from the interior region 40 of ion mobility spectrometer 10. Such vent openings may be provided at any of a wide range of locations. By way of example, in one embodiment wherein three (3) carrier gas inlets 23 are provided at 120□ intervals around the ion interface 12, three (3) vents (not shown) are also provided at 120□ intervals around the ion interface 12, but off-set from the carrier gas inlets 34 by about 60□.

The ion mobility spectrometer 10 may also be provided with a data processing system 42. The data processing system 42 is operatively connected to each of the detectors 26 and 30 and receives respective output signals 44 and 46 therefrom. The data processing system 42 processes data contained in the output signals 44 and 46 to produce output data 48. The output data 48 may then be presented on a suitable display system 50. The data processing system 48 and display system 50 may comprise a general purpose programmable computer (e.g., a PC) that contains data processing software suitable for analyzing the data contained in the output signals 44 and 46 and for producing the output data 48. The software may comprise conventional data analysis and processing algorithms utilized by currently available ion mobility spectrometers. Alternatively, other data analysis and processing algorithms, such as the Spectral IDentification Inference Engine (SIDIE), which is available from Idaho National Laboratory of Idaho Falls, Id. (US), could also be used.

The ion mobility spectrometer 10 may be operated as follows to perform ion mobility spectrometry in accordance with the methods described herein. Assuming a suitable sample has been collected, gaseous constituents (represented by arrow 58) of the sample are ionized within an ionization chamber 60. The gaseous constituents 58 of the sample will commonly result in the formation of both positive and negative ions. However, certain gaseous constituents 58 may result in the formation of exclusively either positive ions or negative ions. Regardless of whether the gaseous constituents 58 result in the formation of positive ions, negative ions, or more commonly a combination of both positive and negative ions, ions (not shown) formed within the ionization chamber 60 are then introduced into the ion interface 12 through outlet end 66 of ionization chamber 60.

Before proceeding with the description, it should be noted that it may be desirable or advantageous in certain circumstances to heat the ion mobility spectrometer 10 to drive-off any water present to ensure that it does not form adducts with the ions. Such heating may be accomplished by placing the entire ion mobility spectrometer 10 in an oven (not shown) or other heated atmosphere. Alternatively, the ion mobility spectrometer 10 could be heated by means of electrically resistive tape secured to the spectrometer 10. Generally speaking, the ion mobility spectrometer 10 should be heated to at least about 110□C or so to ensure that any water present will be evaporated. In addition, heating of the ion mobility spectrometer 10 may also have the added benefit of helping to clean the ion mobility spectrometer 10 of any undesirable materials which may have remained in the ion mobility spectrometer 10 from previous uses. Heating for cleaning purposes may be conducted at higher temperatures depending on the particular materials that are to be removed by heating.

Continuing now with the description, the voltage source 52 is operated to apply the ion-confining voltage function to the ion interface 12. The ion-confining voltage function results in the formation of the quadrupolar electric field 54 (FIG. 4) within the ion interface 12. The quadrupolar electric field 54 confines both positive and negative ions within the ion interface 12. In one embodiment, the quadrupolar electric field 54 is applied (i.e., turned on and off) at a frequency of about 100 Hz. This will allow positive and negative ions introduced through outlet end 66 of ionization chamber 60 to "roll" to the center of the ion interface 12.

The voltage source 52 is also operated to place a voltage potential along the axes 22 and 24 of respective first and second drift chambers 14 and 16. For example, in one embodiment, the voltage source 52 places a voltage potential of about +1500 volts on the distal end 32 of second drift chamber 16, and about −1500 volts on the distal end 28 of first drift chamber 14. The outer electrode 70 of the ion interface 12 is maintained at about 0 volts (e.g., ground potential). With these voltage potentials, the first drift chamber 14 comprises the positive ion drift chamber, whereas the second drift chamber 16 comprises the negative ion drift chamber.

At the appropriate time, the voltage source 52 may be operated to instead apply the ion release voltage function to the ion interface 12. The ion release voltage function causes the quadrupolar electric field 54 to change to the linear electric field 56 (FIG. 5), resulting in the substantially simultaneous release of both positive and negative ions from the ion interface 12. That is, positive ions are released through the positive ion port 18 into the first drift chamber 14, whereas negative ions are released through the negative ion port 20 into the second drift chamber 16 at substantially the same time.

Upon entering the drift chambers 14 and 16, the respective positive and negative ions travel toward the respective distal ends 28 and 32 of the drift chambers 14 and 16 under the influence of the electric fields enclosed thereby. See, for example, FIGS. 10 and 11. Positive ions reaching the distal end 28 of first drift chamber 14 are detected by the first ion detector 26, whereas negative ions reaching the distal end 32 of second drift chamber 16 are detected by the second ion detector 30. The data processing system 42 receives output signals 44 and 46 from the respective current measuring systems 47 and 49 that are operatively associated with the first and second ion detectors 26 and 30 and processes them to produce output data 48. Thereafter, output data 48 may be presented on display system 50.

Having herein set forth preferred embodiments of the present invention, it is anticipated that suitable modifications can be made thereto which will nonetheless remain within the scope of the invention. The invention shall therefore only be construed in accordance with the following claims:

The invention claimed is:

1. An ion mobility spectrometer, comprising:
    an ion interface, said ion interface being operable to hold positive and negative ions in a quadrupolar electric field and to simultaneously release positive and negative ions through respective positive and negative ion ports by changing said quadrupolar electric field to a linear electric field;
    a first drift chamber enclosing an electric field therein, said first drift chamber being operatively associated with the positive ion port of said ion interface;
    a first ion detector operatively associated with said first drift chamber, said first ion detector detecting positive ions from said first drift chamber;
    a second drift chamber enclosing an electric field therein, said second drift chamber being operatively associated with the negative ion port of said ion interface; and
    a second ion detector operatively associated with said second drift chamber, said second ion detector detecting negative ions from said second drift chamber.

2. The ion mobility spectrometer of claim 1, wherein said first and second drift chambers are positioned on opposite sides of said ion interface so that respective axes of said first and second drift chambers are substantially aligned.

3. The ion mobility spectrometer of claim 2, wherein said ion interface comprises a substantially cylindrical body having an axis, the respective axes of said first and second drift chambers being substantially aligned with the axis of the substantially cylindrical body of said ion interface.

4. The ion mobility spectrometer of claim 3, further comprising an ion source operatively associated with said ion interface, said ion source injecting ions substantially radially into the substantially cylindrical body of said ion interface.

5. The ion mobility spectrometer of claim 1, wherein said ion interface comprises a plurality of electrodes therein, said ion mobility spectrometer further comprising a voltage source operatively associated with said ion interface, said voltage source applying voltage functions to the plurality of electrodes to produce a quadrupolar electric field within said ion interface, said quadrupolar electric field holding positive and negative ions within an interior space enclosed by said ion interface.

6. The ion mobility spectrometer of claim 1, wherein said ion interface comprises a plurality of electrodes therein, said ion mobility spectrometer further comprising a voltage source operatively associated with said ion interface, said voltage source applying voltage functions to the plurality of electrodes to produce a linear electric field within said ion interface, said linear electric field simultaneously releasing positive and negative ions from said ion interface.

7. The ion mobility spectrometer of claim 1, wherein said first drift chamber comprises a ferrite material arranged along the axis of said first drift chamber, said ion mobility spectrometer further comprising a voltage source operatively connected to said ferrite material, said voltage source placing a voltage potential across said ferrite material, the voltage potential causing the electric field to vary substantially linearly along the axis of said first drift chamber.

8. The ion mobility spectrometer of claim 1, wherein said second drift chamber comprises a ferrite material arranged along the axis of said second drift chamber, said ion mobility spectrometer further comprising a voltage source operatively connected to said ferrite material, said voltage source placing a voltage potential across said ferrite material, the voltage potential causing the electric field to vary substantially linearly along the axis of said second drift chamber.

9. The ion mobility spectrometer of claim 1, further comprising a data processor operatively associated with said first ion detector and said second ion detector, said data processor receiving respective first and second ion impact signals from said first and second ion detectors.

10. The ion mobility spectrometer of claim 1, wherein said ion interface comprises:
    an outer electrode defining an interior region between first and second opposed open ends;
    a first inner electrode positioned within the interior region of said outer electrode at about the first open end of said outer electrode;
    a second inner electrode positioned within the interior region of said outer electrode at about the second open end of said outer electrode;
    a first end cap electrode positioned at about the first open end of said outer electrode so that the first end cap electrode substantially encloses the first open end of said outer electrode;
    a second end cap electrode positioned at about the second open end of said outer electrode so that the second end cap electrode substantially encloses the second open end of said outer electrode; and
    a voltage source operatively connected to each of said outer electrode, said first and second inner electrodes, and said first and second end cap electrodes, said third voltage source applying voltage functions to each of said electrodes to produce an electric field within an interior space enclosed by said electrodes.

11. The ion mobility spectrometer of claim 10, wherein the voltage functions are selected to produce a quadrupole electric field within the interior space enclosed by said electrodes, said quadrupole electric field substantially confining ions within the interior space.

12. The ion mobility spectrometer of claim 11, wherein the voltage functions are selected to produce a linear electric field within the interior space enclosed by said electrons, said linear electric field allowing ions within the interior space enclosed by said electrodes to be released into said first and second drift chambers.

13. The ion mobility spectrometer of claim 10 wherein the first end of said first drift chamber is operatively associated with said first end cap electrode so that the first end of said first drift chamber receives ions from said ion interface through said first end cap electrode of said ion interface.

14. The ion mobility spectrometer of claim 10, wherein the first end of said second drift chamber is operatively associated with said second end cap electrode so that the first end of said second drift chamber receives ions from said ion interface through said second end cap electrode of said ion interface.

15. The ion mobility spectrometer of claim 10, further comprising an ion source operatively associated with said outer electrode of said ion interface, said ion source injecting ions into the interior space enclosed by said electrodes.

16. A method for performing ion mobility spectrometry, comprising:

holding positive and negative ions in a holding region in a quadrupolar electric field;

simultaneously releasing positive and negative ions from the holding region into respective first and second drift tubes by changing said quadrupolar electric field to a linear electric field;

detecting positive ions arriving at a distal end of the first drift tube; and detecting negative ions arriving at a distal end of the second drift tube.

17. The method of claim 16, further comprising:

establishing a linear electric field along an axis of the first drift chamber before receiving positive ions from said linear electric field; and establishing a linear electric field along an axis of the second drift chamber before receiving negative ions from said linear electric field.

* * * * *